(12) United States Patent
Miller et al.

(10) Patent No.: US 9,464,019 B2
(45) Date of Patent: Oct. 11, 2016

(54) HEAT MANAGEMENT PROCESS

(71) Applicant: Dow Technology Investments LLC, Midland, MI (US)

(72) Inventors: Glenn A. Miller, South Charleston, WV (US); Irvin B. Cox, St. Albans, WV (US); Morteza Mokhtarzadeh, Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/889,231

(22) PCT Filed: Jun. 18, 2014

(86) PCT No.: PCT/US2014/042835
§ 371 (c)(1),
(2) Date: Nov. 5, 2015

(87) PCT Pub. No.: WO2014/209696
PCT Pub. Date: Dec. 31, 2014

(65) Prior Publication Data
US 2016/0107971 A1    Apr. 21, 2016

Related U.S. Application Data

(60) Provisional application No. 61/839,901, filed on Jun. 27, 2013.

(51) Int. Cl.
C07C 45/50    (2006.01)
C07C 45/81    (2006.01)
B01D 53/74    (2006.01)

(52) U.S. Cl.
CPC ............... *C07C 45/81* (2013.01); *C07C 45/50* (2013.01); *B01D 53/74* (2013.01)

(58) Field of Classification Search
CPC ......... C07C 45/50; B01J 19/14; B01D 53/74
USPC ...................................................... 568/451
See application file for complete search history.

(56) References Cited

U.S. PATENT DOCUMENTS

| | | |
|---|---|---|
| 3,527,809 A | 9/1970 | Pruett et al. |
| 4,040,806 A | 8/1977 | Kennedy |
| 4,210,426 A | 7/1980 | Sridhar |
| 4,247,486 A | 1/1981 | Brewester et al. |
| 4,287,369 A | 9/1981 | Harris et al. |
| 4,593,127 A | 6/1986 | Bunning et al. |
| 4,599,206 A | 7/1986 | Billig et al. |
| 4,668,651 A | 5/1987 | Billig et al. |
| 4,716,250 A | 12/1987 | Abatjoglou et al. |
| 5,001,274 A | 3/1991 | Bunning |
| 5,367,106 A | 11/1994 | Unruh et al. |
| 5,426,238 A | 6/1995 | Mori et al. |
| 5,463,137 A | 10/1995 | Ramachandran et al. |
| 5,483,201 A | 1/1996 | Bortolini |
| 5,675,041 A | 10/1997 | Kiss et al. |
| 5,741,944 A | 4/1998 | Bryant et al. |
| 6,100,432 A | 8/2000 | Borgel et al. |
| 6,414,202 B1 | 7/2002 | Baker et al. |
| 6,822,122 B2 | 11/2004 | Richter et al. |
| 6,864,391 B2 | 3/2005 | Krokoszinski et al. |
| 7,196,230 B2 | 3/2007 | Peng et al. |
| 7,208,635 B2 * | 4/2007 | Richter ................... C07C 45/50 568/454 |
| 7,405,329 B2 * | 7/2008 | Beadle ..................... C07C 45/50 568/451 |
| 7,446,231 B2 | 11/2008 | Peterson et al. |
| 7,863,487 B2 | 1/2011 | Eisenschmid et al. |
| 8,461,366 B2 | 6/2013 | Tulchinsky et al. |
| 2005/0119509 A1 | 6/2005 | Richter et al. |
| 2010/0044628 A1 | 2/2010 | Brammer et al. |

FOREIGN PATENT DOCUMENTS

| | | |
|---|---|---|
| CN | 101774912 A | 7/2010 |
| GB | 1387657 A | 3/1975 |
| JP | 4122528 B2 | 7/2008 |
| WO | 2010/021863 A1 | 2/2010 |
| WO | 2010/081526 A1 | 7/2010 |
| WO | 2010/115509 A1 | 10/2010 |

OTHER PUBLICATIONS

Beller et al., Progress in hydroformylation and carbonylation, Journal of Molecular Catalysis A, 104 (1995), pp. 17-85.
PCT/US2014/042835, International Search Report & Written Opinion mailed Sep. 19, 2014.
PCT/US2014/042835, International Preliminary Report on Patentability mailed Jan. 7, 2016.

* cited by examiner

*Primary Examiner* — Sikarl Witherspoon

(57) ABSTRACT

A method of managing the heat of a chemical reaction process.

12 Claims, 1 Drawing Sheet

HEAT MANAGEMENT PROCESS

CROSS-REFERENCE TO RELATED APPLICATIONS

This application claims priority from provisional application Ser. No. 61/839,901, filed Jun. 27, 2013, which is incorporated herein by reference in its entirety.

BACKGROUND OF THE INVENTION

The invention relates to heat management in a chemical process.

There are a number of chemical processes that involve hydrogen at elevated pressure, including hydroformylation, hydrocarbonylation, hydroaminomethylation, and hydrocyanation of olefins. Each of these must deal with the presence of feed stream impurities, which can include $N_2$, Ar, $CO_2$, methane, higher alkanes, water, and the like. These impurities typically are purged from the process in a vent stream.

For example, the hydroformylation of olefins, such as propylene, is carried out industrially in a continuous process in that the olefin, carbon monoxide and hydrogen are reacted in a hydroformylation reactor in the presence of a hydroformylation catalyst. The output from the reactor comprises the hydroformylation products (aldehydes, alcohols) and generally significant amounts of unreacted olefin that must be separated off and recirculated to the hydroformylation reactor. When olefins are subjected to hydroformylation, i.e., an Oxo reaction at 50° C. to over 200° C. and pressures as low as 3 bar and as high as over 200 bar, gas mixtures are obtained in addition to the liquid reaction products such as aldehydes and alcohols. These gas mixtures consist of the unconverted reactants and also of alkanes from the olefin feed as an impurity and from side reaction hydrogenation of the olefin. Conventional olefin hydroformylation reaction schemes must allow for venting of inerts such as $N_2$, Ar, $CH_4$, alkanes, $CO_2$ and the like. In the case of propylene hydroformylation, these gas mixtures have been burned as off-gases, since the recovery of olefin, CO and $H_2$ from the off-gases is not cost effective. These gas mixtures together with the i-butyraldehyde obtained as an isomeric by-product, have been partially oxidized to produce the syngas, (i.e., carbon monoxide and hydrogen), olefin, and hydrogen required for the hydroformylation. However, after the enormous increase in the price of propylene, the conversion of valuable propylene to syngas is no longer economical.

In general, it would be desirable to recirculate the unreacted olefin back to the reactors to get maximum conversion. However, this recirculation also recycles the inert propane that is present as an impurity in the feed propylene, or formed by side reactions in the hydroformylation reactor. To prevent the propane concentration in the hydroformylation reactor from rising continually and reaching values at that the hydroformylation reaction ceases, a sub-stream of the recirculated propylene-containing stream must be continually bled off from the process in order to remove the inerts and propane.

However, unreacted propylene also is removed from the system by the bleed stream. To keep propylene losses small, a propylene feed of high purity is generally used. Thus, hydroformylation is usually carried out using a propylene feed having a purity of about 99.5%, with the remainder consisting essentially of propane. This grade of propylene is referred to as "polymer grade propylene." Such high purity propylene is sold at significantly higher prices than propylene of lower purity. For example, "chemical grade propylene" containing from about 3 to 7% by weight of propane is significantly cheaper than polymer grade propylene.

For the reasons mentioned above, a propylene feed having a relatively high proportion of propane cannot be used in an industrial hydroformylation process without taking appropriate measures.

Reactor vent streams contain valuable olefin, syngas, and product, that is lost to the fuel header or flare. The prior art has many ways of recovering reactants. Examples of secondary reactors on these vents to maximize conversion are known; see, e.g., GB 1,387,657, U.S. Pat. No. 4,593,127, U.S. Pat. No. 5,367,106, U.S. Pat. No. 5,426,238, U.S. Pat. No. 7,405,329, WO 2010/081526 and WO 2010/115509. Nevertheless, a vent purge of inert gases and alkanes is still present.

Significant prior art focuses on recovery of the contained olefin, such as propylene, in these streams, but little attention has been focused on product loss minimization. For example, U.S. Pat. No. 4,210,426 employs an extensive absorption/desorption scheme with up to 3 columns to extract the olefin from the vent stream. This capital intensive process is complex. There is no mention of recovering any contained aldehyde product.

Separation processes that require a foreign substance as a recovery agent are known, using agents such as diethylpropionamide, methanol, aromatic compounds, acetonitrile, dimethoxytetraethylene glycol, hydrocarbons and aldehyde heavies. However, these processes have a considerable disadvantage, in that the gases recovered from the off-gases require careful purification to remove the particular recovery agent before the gases are re-employed in the hydroformylation process. It is not clear how an aldehyde product could be recovered from these systems without expensive refining.

U.S. Pat. No. 5,001,274, U.S. Pat. No. 5,675,041, U.S. Pat. No. 6,822,122, U.S. Pat. No. 6,100,432, and JP 4122528 discuss using vent scrubbers and vent distillation schemes to recover unreacted olefins. Again, these complex schemes are focused on recovering the olefin and only U.S. Pat. No. 5,001,274 has any discussion of recovering any contained aldehyde or alcohol product in the vent stream. However, U.S. Pat. No. 5,001,274 also captures inerts such as alkanes, which may interfere with the inert purge.

Pressure-swing absorption (PSA) and related technologies to separate propylene and recycle it to the hydroformylation zone are taught by U.S. Pat. No. 5,463,137 and U.S. Pat. No. 5,483,201. Membrane technologies are also applicable, as taught in U.S. Pat. No. 6,414,202. CN 101774912 A1 teaches using PSA to recover syngas to be recycled back to the hydroformylation zone. All of these are capital intensive, and the complex mixture of polar aldehydes and their interaction with the other components tend to interfere with these technologies, especially for long term use. The alternating adsorption and desorption cycles require periodic pressure and/or temperature changes. The equipment required for PSA are complicated and susceptible to malfunctions.

Refrigeration to cool the vent stream to condense the product is an available option, but refrigeration is expensive and high maintenance; see, e.g., U.S. Pat. No. 4,287,369 Ammonia, a common refrigerant, is reactive with aldehydes. Thus, any leaks could have highly undesirable consequences. Conventional cooling water is typically around 40° C. and a significant amount of aldehyde can still be present due to a significant vapor pressure at that temperature. The use of propane as a coolant is known. For example, in U.S. Pat. No. 4,210,426, purified propane decompression is used to cool the reflux condenser in an aldehyde-propane distillation column. In this case, the condenser is used to recycle the absorbent fluid. The propane stream is quite pure, as hydrogen, inert gases, etc. were removed at an earlier stage. This process requires two columns to purify the propane before it is used as a refrigerant.

U.S. Pat. No. 6,864,391 discloses a process in which the vent stream is oxidized to convert the contained olefin into other more readily isolated products, such as the corresponding acrylic acid, but only after extensive refining to remove traces of aldehyde from the stream.

All these processes are unsuitable for the recovery of aldehyde product from the off-gases from the hydroformylation of propylene, since they are much too expensive.

It would be desirable to have a simple and economical process for the recovery of products, such as aldehydes, from reactor vent streams.

SUMMARY OF THE INVENTION

The process of the invention is such a process comprising:
a) providing a vapor phase vent stream from a chemical process that employs organics and $H_2$, the stream comprising an uncondensed product, organics, hydrogen and inert gases,
b) cooling the vent stream in a cross-exchanger to form a cooled stream,
c) separating the cooled stream into a crude product liquid stream and a gas phase stream,
d) lowering, in a depressurization device, the pressure of the gas phase stream to form a cooled gas phase stream, wherein the pressure drop across the depressurization device is greater than 1 bar and the organics to $H_2$ weight ratio of the cooled gas phase stream is greater than 8:1, and
e) using the cooled gas phase stream in the cross exchanger to cool the vapor phase vent stream.

Surprisingly, the process of the invention allows significant quantities of valuable product to be recovered from the vent stream in a cost-effective manner.

DETAILED DESCRIPTION OF THE INVENTION

Figure 1:
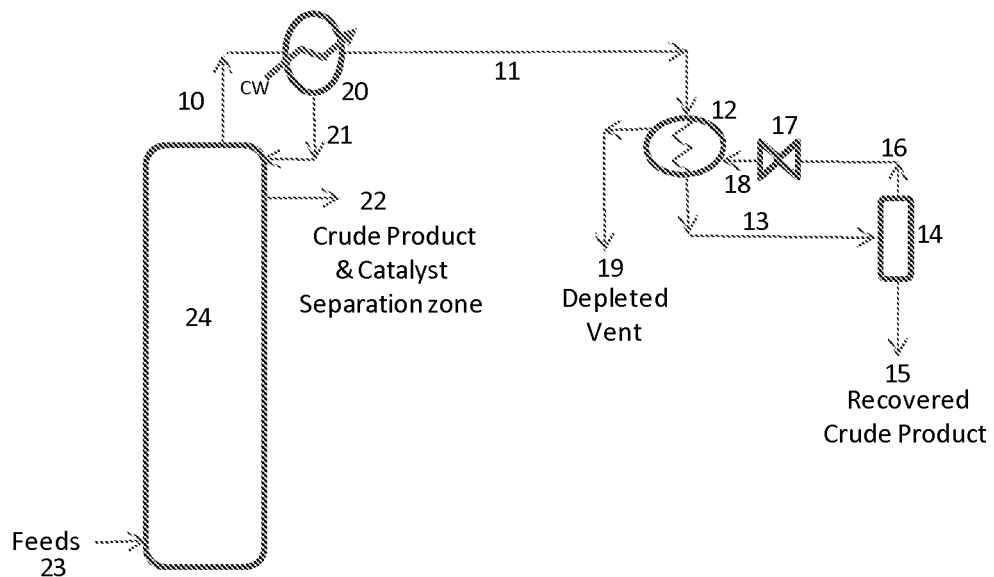
FIG. 1 is a schematic of a chemical reaction process.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application.

For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The process of the invention operates on a vapor phase effluent stream obtained from a chemical reaction process. For convenience, the following description will focus on the hydroformylation process as an illustrative chemical process.

The olefin, carbon monoxide and hydrogen starting materials for the hydroformylation reaction are commercially available and are well known to those skilled in the art. Similarly, those skilled in the art are familiar with hydroformylation vapor phase effluent streams comprising uncondensed aldehyde product, inert gases, and unreacted starting materials.

Carbon monoxide and hydrogen are usually used in the form of a mixture, namely synthesis gas (syngas). The composition of the syngas can vary within a wide range. The molar ratio of carbon monoxide to hydrogen is generally from 5:1 to 1:5, preferably from 2:1 to 1:2, in particular about 45:55.

The propylene feed that is suitable as starting material for hydroformylation may comprise a proportion of propane in addition to propylene. It contains, for example, from 0.5 to 40% by weight, preferably from 2 to 30% by weight and in particular from 3 to 10% by weight, of propane. While any grade of propylene can be employed, including polymer grade, a preferred example is "chemical grade propylene," that contains from 3 to 10% by weight of propane. It is obtained, for example, by reaction of naphtha or natural gas in a steam cracker and subsequent work-up by distillation. A further example of a suitable propylene feed is "refinery grade propylene" that has a propane content of from 20 to 30%.

The catalyst used in the hydroformylation reactors is not particularly critical for the invention. Suitable hydroformylation catalysts are the customary transition metal compounds and complexes that are known to those skilled in the art and can be used either with or without co-catalysts. The transition metal is preferably a metal of transition group VIII of the Periodic Table, in particular Co, Ru, Rh, Pd, Pt, Os or Ir, especially Rh, Co, Ir or Ru. Particularly preferred hydroformylation catalysts for the hydroformylation of propylene, butene, and other 1-olefins are phosphorus-containing rhodium catalysts such as $RhH(CO)_2(PPh_3)_2$ or $RhH(CO)(PPh_3)_3$. Suitable hydroformylation catalysts are described, for example, in Beller et al., *Journal of Molecular Catalysis A*, 104 (1995), pp. 17-85, U.S. Pat. No. 3,527,809, U.S. Pat. No. 4,247,486, U.S. Pat. No. 4,283,562, U.S. Pat. No. 4,599,206, U.S. Pat. No. 4,668,651, U.S. Pat. No. 4,716,250, U.S. Pat. No. 5,741,944, U.S. Pat. No. 7,196,230, U.S. Pat. No. 7,446,231, U.S. Pat. No. 7,863,487, US 2010/0044628, WO 2010/021863 and U.S. Pat. No. 8,461,366. Other suitable catalyst systems include Rh-phosphites, Rh-phosphonites, Rh-polyorganophosphites, Rh-phosphoramidites, and the like. Similarly, water-based rhodium catalysts with ionic phosphines, such as trisulfonated-triphenylphosphine and cobalt or phosphine-modified cobalt catalysts, can be used.

Known industrial processes provide a variety of vent streams, the compositions of which, in general, are not particularly critical to the success of the process of the invention as long as certain preconditions are met. The vent stream of the invention may contain product, inert gases, water vapor, and unreacted reactants, and is at elevated pressure. A suitable vent stream advantageously comprises the hydroformylation product, e.g., butyraldehyde and/or butanol, and unreacted propylene, unreacted syngas, propane and inert gases. The product will be at saturation concentration in the vapor stream exiting the process (or an intermediate reflux condenser). The primary purposes of the vent stream are to remove inert gases and to control pressure.

For the purposes of this invention, the term "organics" means $C_nH_mO_p$ (where n is from 1-5, m is from 2 to 12, and p is zero or one), excluding the desired product of the chemical process. Examples of organics include unreacted reactants, organic feed impurities, and, in the case of reactions involving hydrogen and olefins, hydrogenated non-product olefins.

The amount of hydrogen in the reactor is controlled to maximize the reaction yield (to avoid excessive olefin hydrogenation). Thus, the weight ratio of organics to hydrogen in the vent advantageously is greater than 8:1. This ratio preferably is greater than 10:1, and most preferably is greater than 20:1 in the vent stream prior to decompression (e.g., stream 11 of FIG. 1).

The process of the invention can employ a low capital, low maintenance system, and captures a large portion of the available aldehyde without also capturing inerts (e.g., alkanes, $CO_2$, etc.) that will interfere with inert purging requirements. Downstream processing of the vent stream via known technologies to recover the unreacted reactants, such as olefins, from the other inerts can still be done without the interference from a substantial amount of the product recovered via the process of the invention.

The amount of pressure drop available will also have an impact on the amount of cooling available. While compressors can be used to increase the pressure prior to the decompression (with a heat exchanger in between), this greatly increases the complexity and capital expense. Similarly, vacuum on the downstream side of the decompression also increases complexity and capital expense but may find use in specialized cases.

In one embodiment of the invention, the process is an improved hydroformylation process that comprises:

1) contacting in a reaction zone a $C_2$-$C_5$ olefin-containing feed with carbon monoxide and hydrogen in the presence of a hydroformylation catalyst under reaction conditions sufficient to form at least one hydroformylation product of the olefin, thereby producing a vent stream, 2) cooling the vent stream comprising uncondensed aldehyde product, inert gases, syngas, alkane and unreacted olefin in a cross-exchanger to form a cooled stream, 3) forwarding the cooled stream to a vapor liquid separator to separate the cooled stream into a crude product liquid stream and a gas phase stream, 4) lowering, in a depressurization device, the pressure of the gas phase stream to form a cooled gas phase stream, wherein the pressure drop across the depressurization device is greater than 1 bar and the organics to $H_2$ weight ratio of the cooled gas phase stream is greater than 8:1, and 5) using the cooled gas phase stream in the cross exchanger to cool the vapor phase vent stream.

One embodiment of the invention is represented in FIG. 1. An off-gas vent stream (10) from one or more conventional hydroformylation reactors (24) is passed through an optional knockout pot(s) (not shown) or conventional condenser (20) to create a condensate stream (21) and the vent stream (11). Stream (21) returns mixed aldehyde product contained therein back to the reaction zone. Stream (21) comprises condensed product and condensed organics. The vent stream (11) is passed through a cross exchanger (12) (preferably of counter-flow design) to obtain a cooled stream (13), which is sent to a gas-liquid separator (14). Stream 11 comprises uncondensed product, uncondensed organics, hydrogen and inert gases. The gas-liquid separator (14) produces a gas stream (16), still at elevated pressure, and a recovered product stream (15). Stream (16) is sent through a decompression valve (17) to produce a decompressed gas stream (18), which is sent into the "coolant" side of cross exchanger (12). The decompressed gas stream (18) absorbs the heat from the incoming gas on the "process" side, thereby cooling stream (11). The depressurized, depleted vent gas stream (19) after the heat exchanger is sent to either flare, a fuel header, or other downstream processing to recover olefin.

Similar schemes can be applied to vent streams from vaporizers or other processing equipment such that a stream analogous to stream (11) above is generated that will meet the requirements set forth herein.

For the purposes of the invention, the term "cross exchanger" means a heat exchanger that exchanges heat between at least 2 process streams having different properties, e.g., temperature and/or pressure. The cross exchanger can be any suitable heat exchanger including, for example shell and tube, spiral, and plate and frame heat exchangers. The flow through the exchanger can be, for example, countercurrent, co-current or cross current.

Figure 2:
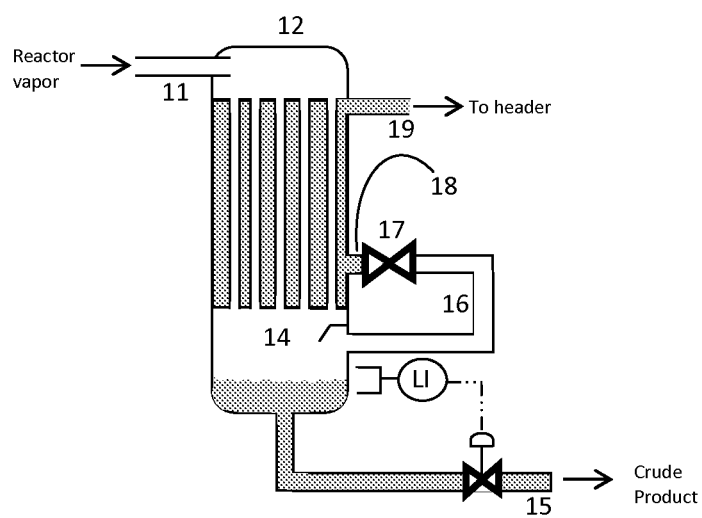
FIG. 2 is a schematic of a cross exchanger with a depressurization device.

One embodiment of the cross exchanger employed in the invention is represented in FIG. 2. The complexity of the process can be greatly simplified by combining the cross exchanger and gas-liquid separator into a single unit as shown in FIG. 2. Stream (11) enters the top of a tube-and-shell heat exchanger and the gases pass through the inside of the tubes. Condensed liquid forms on the inner surface of the tubes and flows downward. The gas and liquid separates in the bottom head area (14) and the liquid level is maintained by a liquid-level controller, using equipment and techniques well known to those skilled in the art. The separated gas stream (16) passes to the shell side via decompression valve (17) and provides the cooling to the tubes. The decompressed gas stream (19) then exits the exchanger. The collected crude product stream (15) is sent to product recovery (typically combined with the conventional product recovery of the relevant process).

For the system shown in FIG. 2, demisters or baffles may be installed where stream (16) exits cross exchanger (12) to prevent entrainment of liquid into stream (16). Within the tube area after the decompression valve, distribution, diverter or impingement plates may be used to aid in distribution of cooling. More than one decompression valve can be used as well. Liquid-level controller technology is well known and is used to minimize backpressure from vaporized aldehyde and downstream gases. The flow of stream (15) is controlled either by pumping it to downstream refining or, preferably, simply allowing it to flow into lower pressure points in the system, such as the product collection pot after a low pressure vaporizer in the conventional product-catalyst separation zone.

The coolant gas can be on the shell or process side, depending on design considerations well known to those skilled in the art of heat exchanger design. The entire system advantageously is well insulated from outside warming, e.g., at locations above the bottom valve and after stream (19) leaves the top of the exchanger.

It is recognized that, at startup, the process equipment will all be at similar pressures and it will take a small amount of time for a pressure drop (and hence, cooling) to be developed. This will not impact the utility of the invention, as this situation will quickly reach steady state operating conditions wherein the cooling and product collection will occur without operator actions.

The process of the invention can be used within the typical range of temperatures, pressures, and compositions found in chemical reaction systems. For example, in hydrocarbonylation, hydroaminomethylation, hydrocyanation, and hydroformylation vents, the temperature of the vent stream can be from 50 to 200° C., and the pressure can be from 10 to 700 bar.

The temperature in the hydroformylation reaction is generally in a range from 50 to 200° C., preferably from about 60 to 190° C., in particular from about 90 to 190° C. The reaction is preferably carried out at a pressure in the range from about 10 to 700 bar, more preferably from 15 to 200 bar, in particular from 15 to 60 bar. The reaction pressure can be varied as a function of the activity of the hydroformylation catalyst used. Hydroaminomethylation processes generally run under the same conditions as hydroformylation processes.

Similarly, hydrocarbonylation reactions are generally run in a range from 100-320° C. and 10-250 bar. Where the alcohol is the desired product, the process is carried out preferably at 90-130° C. and 10-15 bar but if the carboxylic acid is desired, these carbonylations are preferably carried out at 200-240 bar and 270-320° C. Koch carbonylation processes are typically run in a range of 20-300° C. and pressures from 20-300 bar. These carbonylation reactions generate hydrogen in situ that will be present in the vent stream.

Hydrocyanation processes generally run from 80-210° C. and from 25-200 bar, preferably between 80-130° C. and 40-200 bar.

Suitable pressure-rated reaction apparatuses for carrying out the hydroformylation are known to those skilled in the art. They include the generally customary reactors for gas-liquid reactions, e.g., stirred vessels, gas recycle reactors, bubble columns, etc., which may be further divided by means of internals.

A key and surprising feature of the invention is that the decompression cooling must be applied to the high-pressure gas before decompression and most of the product must be removed prior to feeding the depleted gas to the decompression device. While this increases the concentration of hydrogen gas in the decompression step, the overall final cooled gas temperature is lower (thus heat exchange is improved) that is counter-intuitive.

SPECIFIC EMBODIMENTS OF THE INVENTION

The following examples are given to illustrate the invention and should not be construed as limiting its scope.

Example 1

Referring to FIG. 1, an off-gas vent stream from a conventional propylene hydroformylation reactor (stream (10)) comprises mixed butyraldehyde product as well as propane and inert gases, unreacted propylene and unreacted syngas. The stream is passed through a conventional water-cooled condenser (20) to condense and recycle the mixed butyraldehyde product (21) back to the reactor (24). The resulting vent off-gas stream (11) is passed through a counter-flow heat exchanger (12) to a gas-liquid separator (14). The gas stream (16), still at elevated pressure, is separated from the recovered product stream (15) and sent through a decompression valve (17) directly into the "coolant" side of the heat exchanger (12). The decompressed gases (18) absorb heat from the incoming gas on the "process" side, cooling it, and liquid aldehyde condenses and is collected in the gas-liquid separator (14). The depressurized gas stream (19) from the heat exchanger (12) is then sent to either a flare or a fuel header. Table 1 shows that going from conventional hydroformylation reactor pressures to a typical fuel header pressure (6 bar) or to flare (1.6 bar) recovers 48% and 54%, respectively, of the contained butyraldehydes and minimal amounts of propane. The temperature and organics:$H_2$ ratio of stream (18) is 20.4° C. and 84:1, respectively for the fuel header case and 15° C. and 83:1, respectively, for the flare header case.

TABLE 1

Results of Ex. 1

| | Fuel Header Case | | | | Flare Header Case | | |
|---|---|---|---|---|---|---|---|
| | Reactor off-gas | Depleted off-gas | Recovered Product | % Recovered | Depleted off-gas | Recovered Product | % Recovered |
| Mass Flow (kg/hr) | (11) | (19) | (15) | | (19) | (15) | |
| $H_2$ | 19.8 | 19.8 | 0.0 | 0% | 19.8 | 0.0 | 0% |
| $N_2$ | 220.9 | 220.7 | 0.2 | 0% | 220.6 | 0.3 | 0% |
| CO | 74.2 | 74.2 | 0.1 | 0% | 74.1 | 0.1 | 0% |
| $CH_4$ | 131.8 | 131.5 | 0.3 | 0% | 131.4 | 0.4 | 0% |
| $CO_2$ | 2.9 | 2.9 | 0.0 | 1% | 2.9 | 0.0 | 1% |
| Propylene | 460.1 | 444.4 | 15.7 | 3% | 439.3 | 20.8 | 5% |
| Propane | 1122.1 | 1082.3 | 39.8 | 4% | 1068.7 | 53.4 | 5% |
| Isobutyraldehyde | 14.3 | 8.5 | 5.8 | 41% | 7.7 | 6.7 | 47% |
| N-Butyraldehyde | 71.7 | 36.3 | 35.3 | 49% | 32.1 | 39.5 | 55% |
| Total aldehyde Overall | | | | 48% | | | |
| Temperature ° C. | 40 | 39 | 31 | | 38.3 | 29.5 | |
| Pressure bar | 18 | 6 | 18 | | 1.65 | 18 | |

Comparative Experiment A (not an Embodiment of the Invention):

The reactor off gas stream (11) of Example 1 is flashed from 18 to 6 bar in a simple flash drum. The organics:$H_2$ ratio from 87:1 and vapor temperature drops to 28.7° C. but no liquid is obtained.

Removing the liquid aldehyde before the decompression in Example 1 allows for an 8.3° C. lower temperature for the cooling gas compared to C.E. A. Removing the aldehyde from the stream before the decompression device in Example 1 decreases the organics:$H_2$ ratio from 87:1 to 83:1 for the flare header case, yet the vent gas temperature is still lower than the higher organics:$H_2$ ratio case of C.E. A.

Example 2

The procedure of Example 1 is followed except that ethylene is the olefin; thus, propionaldehyde is the desired product. The stream (18) temperature is 31.9° C. and the organics:$H_2$ ratio is 16:1. Due to the high reactivity of ethylene, there is less olefin and alkane in the vent stream and the percentage of hydrogen has increased such that the temperature drop has been substantially reduced, yet 9% of the contained aldehyde product is recovered. The results are shown in Table 2. Adjustments to the hydroformylation reactor conditions to drop the contained hydrogen content will increase the recovery.

TABLE 2

Results of Ex. 2

|  | Reactor off-gas | Depleted off-gas | Recovered Product | % Recovery |
|---|---|---|---|---|
| Mass Flow (kg/hr) | (11) | (19) | (15) |  |
| $H_2$ | 2.9 | 2.9 | 0 | 0% |
| $N_2$ | 30.0 | 30.0 | 0.0 | 0% |
| CO | 40.3 | 40.3 | 0.0 | 0% |
| $CO_2$ | 1.2 | 1.2 | 0.0 | 0% |
| $CH_4$ | 35.7 | 35.7 | 0.0 | 0% |
| $C_2H_4$ | 5.0 | 5.0 | 0.0 | 0% |
| $C_2H_6$ | 6.5 | 6.5 | 0.0 | 0% |
| Propionaldehyde | 19.2 | 17.4 | 1.7 | 9% |
| Water | 0.01 | 0.01 | 0.00 |  |
| Temperature ° C. | 40 | 38.3 | 37.5 |  |
| Pressure bar | 19.28 | 1.6 | 19.28 |  |

Example 3

The procedure of Example 1 is followed except that 1-butene is the olefin; thus, mixed valeraldehydes are the desired product. The stream (18) temperature is 32.7° C. and the organics:$H_2$ ratio is 15:1. The results are given in Table 3.

TABLE 3

Results of Ex. 3

|  | Reactor off-gas | Depleted off-gas | Recovered Product | % Recovered |
|---|---|---|---|---|
| Mass Flow (kg/hr) | (11) | (19) | (15) |  |
| $H_2$ | 6.9 | 6.9 | 0.0 | 0% |
| $N_2$ | 15.4 | 45.4 | 0.0 | 0% |
| CO | 29.6 | 29.5 | 0.1 | 0% |
| $CH_4$ | 13.4 | 13.34 | 0.0 | 0% |
| 1-Butene | 49.0 | 47.7 | 1.3 | 3% |
| 2-Butene | 33.5 | 32.4 | 1.1 | 3% |
| Butane | 12.3 | 11.9 | 0.4 | 3% |
| IsoValeraldehyde | 0.1 | 0.0 | 0.0 | 21% |
| Valeraldehyde | 1.6 | 1.2 | 0.5 | 28% |
| Total Aldehyde |  |  | Overall | 27% |
| Temperature ° C. | 40 | 38.4 | 38 |  |
| Pressure bar | 15.84 | 1.6 | 15.84 |  |

The preceding data demonstrate the unexpected result of the process of the invention, in that hydrogen has an extremely strong inverse J-T effect (it heats upon decompression) at the temperatures and pressures that are found in hydroformylation systems, and this effect would be expected to cancel out any temperature drop upon depressurizing the stream.

What is claimed is:

1. A process comprising:
    a) providing a vapor phase vent stream from one or more hydroformylation reactors that employs organics and hydrogen, the stream comprising an uncondensed product, organics, hydrogen and inert gases,
    b) cooling the vent stream in a cross-exchanger to form a cooled stream,
    c) separating the cooled stream into a crude product liquid stream and a gas phase stream,
    d) lowering, in a depressurization device, the pressure of the gas phase stream to form a cooled gas phase stream, wherein the pressure drop across the depressurization device is greater than 1 bar and the organics to $H_2$ weight ratio of the cooled gas phase stream is greater than 8:1, and
    e) using the cooled gas phase stream in the cross-exchanger to cool the vapor phase vent stream.

2. The process of claim 1 further comprising, prior to step a), at least partially condensing a reactor effluent vapor phase stream to form a condensate and the vapor phase vent stream.

3. The process of claim 1 wherein the process is a hydroformylation process, which comprises contacting in a reaction zone a $C_2$-$C_5$ olefin-containing feed with carbon monoxide and hydrogen in the presence of a hydroformylation catalyst under reaction conditions sufficient to form at least one hydroformylation product of the olefin.

4. The process of claim 1 wherein the cross exchanger is a shell and tube heat exchanger.

5. The process of claim 2 wherein the condensate is at least partially recycled to the reaction zone.

6. The process of claim 1 wherein the separation of step c) is conducted in the cross exchanger.

7. The process of claim 1 wherein the organics to $H_2$ weight ratio of the vent stream is greater than 10:1.

8. The process of claim 1 wherein the organics to $H_2$ weight ratio of the vent stream is greater than 20:1.

9. The process of claim 1 wherein the pressure drop across the depressurization device is greater than 5 bar.

10. The process of claim 1 wherein the pressure drop across the depressurization device is greater than 10 bar.

11. The process of claim 1 wherein the pressure drop across the depressurization device is greater than 20 bar.

12. A process comprising:
    a) providing a vapor phase vent stream from one or more hydroformylation reactors that employs organics and hydrogen, the stream comprising an uncondensed product, organics, hydrogen and inert gases,
b) cooling the vent stream in a cross-exchanger to form a cooled stream,
c) separating the cooled stream into a crude product liquid stream and a gas phase stream,
d) lowering, in a depressurization device, the pressure of the gas phase stream to form a cooled gas phase stream, wherein the pressure drop across the depressurization device is greater than 1 bar and the organics to $H_2$ weight ratio of the cooled gas phase stream is greater than 8:1,
e) using the cooled gas phase stream in the cross-exchanger to cool the vapor phase vent stream, and
f) after cooling the vapor phase vent stream, sending the gas phase stream to a flare or a fuel header.

* * * * *